United States Patent
Mombarg

(10) Patent No.: US 8,968,744 B2
(45) Date of Patent: Mar. 3, 2015

(54) AQUEOUS COMPOSITION COMPRISING A BIOLOGICAL ANTIGEN AND AN ACRYLIC ACID POLYMER

(75) Inventor: Erwin Mombarg, Cuijk (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 14/126,951

(22) PCT Filed: Jun. 26, 2012

(86) PCT No.: PCT/EP2012/062279
§ 371 (c)(1),
(2), (4) Date: Dec. 17, 2013

(87) PCT Pub. No.: WO2013/000876
PCT Pub. Date: Jan. 3, 2013

(65) Prior Publication Data
US 2014/0120135 A1    May 1, 2014

Related U.S. Application Data

(60) Provisional application No. 61/501,866, filed on Jun. 28, 2011.

(30) Foreign Application Priority Data

Jun. 27, 2011 (EP) .................................... 11171448

(51) Int. Cl.
*A61K 39/00* (2006.01)
*A61K 39/02* (2006.01)
*A61K 39/12* (2006.01)
*A61K 45/00* (2006.01)
*A61K 39/39* (2006.01)
*A61K 9/00* (2006.01)
*A61K 47/32* (2006.01)

(52) U.S. Cl.
CPC ............... *A61K 39/39* (2013.01); *A61K 9/0019* (2013.01); *A61K 47/32* (2013.01)
USPC ................... 424/184.1; 424/204.1; 424/234.1; 424/278.1

(58) Field of Classification Search
None
See application file for complete search history.

(56) References Cited

U.S. PATENT DOCUMENTS 3,178,350 A    4/1965    Lund
3,920,811 A    11/1975    Lund

FOREIGN PATENT DOCUMENTS

WO    2010/025469 A1    3/2010

OTHER PUBLICATIONS

Nony, et al., "Impact of osmolality on burning sensations during an immediately after intramuscular injection of 0.5 mil of vaccine suspensions in healthy adults", Vaccine, 2001, pp. 3645-3651, vol. 19.
PCT International Search Report for corresponding PCT Application No. PCT/EP2012/062279, mailed on Jul. 27, 2012.
European Search Report for EP Application No. EP 11 17 1448, dated Nov. 17, 2011.

*Primary Examiner* — Albert Navarro

(57) ABSTRACT

The current invention pertains to an aqueous composition containing a biological antigen and an acrylic acid polymer, wherein the composition comprises an electrolyte to provide an osmolarity higher than the osmolarity of a 0.9% (w/v) sodium chloride solution in water. The invention also pertains to the acrylic acid polymer for use in a one shot vaccine against porcine circo virus 2 (PCV2) and optionally *Mycoplasma hyopneumoniae* and in an aqueous composition for reducing fever induced by the biological antigens present in the aqueous composition when the composition is administered to a subject animal.

15 Claims, No Drawings

AQUEOUS COMPOSITION COMPRISING A BIOLOGICAL ANTIGEN AND AN ACRYLIC ACID POLYMER

CROSS-REFERENCE TO RELATED APPLICATIONS

This application is a national stage entry under 35 U.S.C. §371 of PCT/EP2012/062279, filed on Jun. 26, 2012, which claims priority to US Provisional Application No. 61/501,866 filed on Jun. 28, 2011, and EP Application No. 11171448.1, filed on Jun. 27, 2011. The content of PCT/EP2012/062279 is hereby incorporated by reference in its entirety.

The present invention pertains to an aqueous composition comprising a biological antigen and an acrylic acid polymer. The invention also pertains to the acrylic acid polymer for use in a one shot vaccine against porcine circo virus 2 (PCV2) and *Mycoplasma hyopneumoniae* and in an aqueous composition for reducing fever induced by the biological antigens present in the aqueous composition when the composition is administered to a subject animal.

BACKGROUND ART

It is known for example from WO 2010/025469 to provide an aqueous composition (i.e. a composition based on water or another hydrophilic liquid that allows the formation of hydrogen bonds) comprising a biological antigen and an acrylic acid polymer (a biological antigen being an antigen derived from a living organism such as e.g. a bacterium, virus, animal, protist, fungus etc., typically a live or killed microorganism, or a biological molecule, preferably a protein or polysaccharide, derived from the living organism; the term "derived from" encompasses that the biological molecule itself or a precursor thereof is produced by the organism). The acrylic acid polymer in this prior art reference is used as an adjuvant, i.e a non-specific immunostimulating agent included in the composition to favor or amplify a particular process in the cascade of immunological events, ultimately leading to a better immunological response. Acrylic acid polymers have since long been recognized as safe and adequate adjuvants, capable of improving the immunological response to various types of antigens such as live or killed microorganisms, subunits of these organisms or recombinantly produced subunits such as proteins, polysaccharides and other types of molecules. For example, U.S. Pat. No. 3,178,350 already describes the use of an acrylic acid polymer as an adjuvant. These adjuvants are available under the trademark Carbopol™.

A notable property of acrylic acid polymers is that they significantly increase the viscosity of an aqueous composition since they inherently provide linked polymer chains in such compositions. The acid residues of the polymer chains namely may interact by hydrogen-bonding. Although hydrogen bonds are significantly less strong than covalent bonds, this interaction between the polymers chains may have a significant influence on the viscosity of the aqueous solution. This inherent property of acrylic acid polymers, which property is hardly depended on polymer chain length and type of side chains/groups, is widely used in for example creams or lotions where acrylic acid polymers are used as thickening agents. When the linked polymers form a true network of polymer chains throughout the composition (above a certain polymer concentration, typically above 0.2 to 0.5% w/w), and the interstices of the network are filled with the continuous phase, the composition is called a gel. For topical applications of aqueous compositions (such as hand creams, sun tan lotions) this is a preferred state of the composition. For compositions containing biological antigens, which compositions typically are administered via injection, the increase in viscosity is an important disadvantage. Even when the viscosity of the composition rises from about 5-70 mPas (which is typical for an aqueous composition comprising antigens) to about 200 mPas, this is very noticeable when applying the composition by injection (by hand) to a subject animal (the term animal in this specification and appended claims includes a human being). The gelling of the composition is commonly avoided at all times: gelled compositions cannot be readily injected. Therefore in practice, for compositions comprising biological antigens typically 0.1 to a maximum of 0.2% (weight over weight; w/w) of an acrylic acid polymer is applied. Indeed, in WO 2010/025469 which pertains to state-of-the art vaccines, 0.1% w/w of the acrylic acid polymer is applied. An example of a commercially available vaccine comprising an acrylic acid polymer is Suvaxyn™ M. Hyo—Parasuis (available from Pfizer Animal Health), which contains 0.2% (w/w) Carbopol™ 941.

It has been described in the art (U.S. Pat. No. 3,920,811) to add a physiologically acceptable electrolyte (i.e. a compound that ionizes when dissolved or molten to produce an electrically conductive medium), such as the electrolytes mentioned in column 4, lines 28-42 of the '811 patent) to an injectable composition in order to lower the viscosity of the composition to the point where they can be utilized commercially in a practical manner, while at the same time retaining the favorable adjuvant properties. As indicated however clearly in the '811 patent (column 7, lines 3-6), the electrolyte concentration may be as high as that which produces isotonicity in the final injectable solution of the mixture of the adjuvant solution and the biologic antigen. In particular, the actual injectable compositions are typically about one-half isotonic. The reason for this is that it is generally known that hypertonic solutions may provide tissue damage upon injection. Even when the composition is only slightly hypertonic and thus, the ultimate damage may be neglectable, the result of injection is that the animal may have a very uncomfortable feeling at the injection site, which may for example lead to stress, itching, biting etc. Therefore, in order to comply with the generally required safety standards for compositions for administration to animals, each commercially available composition comprising biological antigens and an acryl acid polymer, is at most isotonic with normal body fluid (e.g. serum), i.e. having an osmolarity of a 0.9% (w/v) sodium chloride solution in water (about 300 mOsm/l).

SUMMARY OF THE INVENTION

It is an object of the invention to provide new compositions according to the preamble that have wider applicability.

It has been surprisingly found that in a composition comprising an acryl acid polymer, the use of an amount of electrolyte that provides a hypertonic solution still leads to a composition that complies with generally accepted safety standards. Apparently, without having a clear technical reason for the composition being safe even when it is significantly hypertonic, the presence of the acrylic acid polymer provides for a composition wherein the presence of an excess of electrolyte does not induce a problem, even upon injection of the composition in animal tissue. Without being bound to theory, it is believed that the presence of the polymer in the form of a network of linked polymer chains may constitute a composition wherein a controlled but fast dilution of the excess electrolyte takes place without damaging the surrounding tissue. This indeed contradicts the teaching of the '811 patent which has been the commonly accepted teaching ever since the patent was published. One of the major advantages of the present finding that an excess electrolyte can be used, is that the viscosity of the composition comprising the acrylic acid polymer can be further decreased, thereby allowing easier practical utilization of the composition. Also, the present invention allows the use of far greater amounts of an acrylic acid polymer, even above 0.5% w/w, while still retaining a very low viscosity. The use of such amounts of polymer opens the door to (very) slow-release formulations for the biologic antigens. Given the apparent feature that the electrolyte dilutes fast from the composition upon administration into animal tissue, the viscosity of the composition will immediately after administration increase significantly, and may even form a gelled composition at the site of administration. Inherently, the biological antigens will be released slower from such a gel when compared to release from an aqueous (low viscous) composition as such, depending i.a. on the gel properties. In general, the higher the viscosity, the slower release of antigens is to be expected.

In particular it has been found that an acrylic acid polymer in an aqueous composition comprising biological antigens can be used for reducing fever induced by these biological antigens when the composition is administered to a subject animal. Although a temperature rise of 2° C. within the first 24 hours after injection is generally accepted and regarded safe, a temperature rise below 1° C. is generally favourable. With the compositions according to the current invention, a temperature rise of less the 1° C. or even less then 0.5° C. may be obtained. The reason for this remains unclear but may be linked to the fact that the hypertonic low viscous solution will almost immediately after administration reach a higher viscosity and thus turn into a more or less slow-release formulation. Slow release may result in an immunological response that is less intense, but more prolonged. Although one would expect to see at least some decrease in titre as well, it was very surprisingly found that still high titres can be obtained, even when the fever is decreased significantly. This opens doors to obtain safer vaccines based on antigens that typically induce fever such as for example lipopolysaccharide (LPS) containing antigens as present in many vaccines containing gram-negative bacteria such as for example *Escherichia coli* (*E. coli*), *Salmonella* spp, *Shigella* spp and other Enterobacteriaceae, *Pseudomonas, Moraxella, Helicobacter, Stenotrophomonas, Bdellovibrio*, acetic acid bacteria, *Legionella* and alpha-proteobacteria as *Wolbachia*, cyanobacteria, spirochaetes, green sulfur and green non-sulfur bacteria, *Neisseria gonorrhoeae, Neisseria meningitidis, Moraxella catarrhalis, Haemophilus* spp such as *Haemophilus influenzae, Klebsiella pneumoniae, Legionella pneumophila, Pseudomonas aeruginosa, Proteus mirabilis, Enterobacter cloacae, Serratia marcescens, Helicobacter pylori*, and *Acinetobacter baumannii.*

Apart from the above, it has also been found that the present invention can be advantageously used in a composition containing porcine circo virus 2 (PCV2) antigen and optionally *Mycoplasma hyopneumoniae* antigen and *Lawsonia intracellularis* antigen for providing a vaccine that after one single administration provides an adequate immune response against an infection with porcine circo virus 2 and *Mycoplasma hypneumoniae* and *Lawsonia intracellularis*

It is noted that the present invention also pertains to an injectable composition (in particular a composition having a viscosity less than 200 mPa·s, preferably less than 100 mPa·s) comprising the aqueous composition referred to here-above.

EMBODIMENTS OF THE INVENTION

In an embodiment the osmolarity of the composition is at least 30% higher than the osmolarity of a 0.9% (w/v) sodium chloride solution (i.e. about 400 mOsmol/l or higher). It has been found that even an osmolarity this high can be used without negative side effects at the site of administration. This greatly enhances the freedom in use of the acrylic acid polymer. Even amounts significantly over 0.2% as commonly applied can now be used while retaining a very viscosity.

In an embodiment the osmolarity of the composition is at least 50% higher than the osmolarity of a 0.9% (w/v) sodium chloride solution (i.e. about 450 mOsmol/l or higher). It has been found that even an osmolarity this high can be used without negative side effects at the site of administration. This greatly enhances the freedom in use of the acrylic acid polymer. Even amounts significantly over 0.2% as commonly applied can now be used while retaining a very viscosity.

In a preferred embodiment the composition comprises more than 0.2% (w/w) of the acrylic acid polymer, or even more than 0.5% (w/w) of the acrylic acid polymer. With these amounts of acrylic acid polymer, the composition may be in the form of a viscous gel. By adding the excess electrolyte to the gelled composition, the viscosity may decrease to typical values between 10-70 mPa·s. The composition will thus be easy to apply using a standard hand-held syringe, and after injection, by dilution of the excess electrolyte, will revert to a highly viscous gel. It has been found that such an acrylic acid polymer gel is particularly suitable to obtain high antibody titres against antigens which typically induce fever, while decreasing the resultant fever. A composition which comprises between 0.8% and 1.6% (w/w) of the acrylic acid polymer is particularly preferred. In this embodiment, the excess electrolyte preferable provides an osmolarity of typically more than 2-3 times the osmolarity of normal tissue fluid (0.9% sodium chloride solution), thus more than about 600-900 mOsmol/l. This way, the viscosity before administration can be kept low enough to allow injection. After injection, the electrolyte will dilute and the composition will turn into a gel.

In an embodiment the acrylic acid polymer is a cross linked polymer, preferably using using a polyalkenylether, a polyalcohol and/or a divinylglycol as a cross-linker. Cross-linking the polymer makes the network formation of the polymer chains in the composition less depended on e.g. temperature and pH, simply because part of the network formation is inherently present in the form of covalent cross-links.

In another embodiment the composition comprises an electrolyte comprising a multicharged cation (that is a cation having a higher charge that 1+, typically 2+ or 3+). It has been found that when using a multicharged cation, the viscosity can be more effectively lowered, even when the osmolarity is the same as when using a monocharged (1+) cation. In a preferred embodiment, the cation is present in a concentration up to 0.05M, preferably up to about 0.03M. The amount of cation that can be used depends on the amount of carboxylate groups in the acrylic acid polymer solution. Too much cation will induce precipitation. It has been found that when using up to these amounts of multicharged cation, the viscosity can be very effectively lowered, while retaining safety upon administration of the composition.

In an embodiment the biological antigen is an antigen that upon administration induces fever, i.e. more than 0.5° C., further in particular more than 1.0° C., more than 1.5° C. or even more than 2.0° C. In practice, many antigens upon administration induce some fever. The maximum fever that may be induced is often set by regulatory authorities. In order to comply with such a maximum, in some cases it is necessary to lower the amount of antigen to a sub optimal level, thereby accepting that a non-optimal immunological response is obtained. For preventing the actual disease against which the vaccine should provide protection, this is disadvantageous situation. It has surprisingly been found that by using the composition according to the invention, the fever induced by the antigens may be reduced while retaining the immunological response. Slow-release of the antigens cannot be the sole reason for this effect since one would expect that if the fever is reduced due to a slow release, the immunological response would also be less strong. Applicant however found that by using the present invention, the fever may be reduced while maintaining an adequate immunological response.

In an embodiment the antigen is chosen from the group consisting of a gram-negative bacterium antigen and a circo virus antigen. In a particular embodiment the antigen chosen from the group consisting of *Actinobacillus pleuropneumoniae* antigen, *Haemophilus parasuis* antigen and porcine circo virus 2 (PCV2) antigen. These antigens are particularly known for inducing fever upon administration. By using the present invention, the fever may be reduced significantly while keeping the immunological potency of the composition at an adequate level.

The invention will now be further illustrated using the following examples.

Example 1 shows the effect of an acrylic acid polymer on viscosity

Example 2 pertains to the physical properties of a composition according to the invention, and its safety Example 3 describes the constitution of compositions according to the invention Example 4 shows a vaccination experiment with a composition according to the invention Example 5 shows a second vaccination experiment with a composition according to the invention Example 6 shows a third vaccination experiment with a composition according to the invention Example 7 describes further compositions according to the invention and a method of formulating these compositions.

EXAMPLE 1

Various aqueous isotonic formulations have been made using a cross-linked acrylic acid polymer to assess the effect of the polymer on the viscosity of the composition. The formulations do not comprise antigens (which typically would increase the viscosity). Also, the effect of the addition of an excess amount of a doubly charged electrolyte has been assessed.

All formulations comprised the cross-linked acrylic acid polymer Carbopol 974P (available from BFGoodrich Specialty Chemicals, Cleveland, Ohio). Various amounts of the polymer (0.1 to 1.6% w/w) were solved in an aqueous solution of 0.9% w/v sodium chloride solution. The viscosities of the formulations were measured with a Brookfield laboratory viscometer. The results were as followed:

TABLE 1

Viscosity of various isotonic acrylic acid polymer solutions

| Sample No | Carbopol 974 P w/w | Viscosity mPa · s |
|---|---|---|
| 1 | 0.1 | 3.8 |
| 2 | 0.2 | 5.0 |
| 3 | 0.5 | 70.0 |
| 4 | 0.8 | 214 |
| 5 | 1.6 | 4600 |

It is noted that the aqueous composition of the present invention may be used to make an emulsion with an oil-phase, typically to arrive at a water-in-oil emulsion, an oil-in-water emulsion or a water-in-oil-in-water emulsion. Such an emulsion thus comprises the aqueous composition according to the present invention. Formulating an emulsion will of course impact the viscosity, usually leading to a significant increase. For example, when an oil (e.g. 10% w/v) is emulsified in an aqueous solution having a viscosity of about 3 mPas, the viscosity may increase to about 25 mPa·s or even higher.

In a next experiment, the effect on viscosity by using an excess electrolyte was assessed using a 0.8% Carbopol formulation. To this formulation various amounts of sodium chloride and calcium chloride were added to show the effect on viscosity. The results are depicted in Table 2.

TABLE 2

Viscosity of various acrylic acid polymer solutions

| Sample No | NaCl w/v | $CaCl_2 \cdot 2H_2O$ w/v | Viscosity mPa · s | Osmolarity mOsmol/l |
|---|---|---|---|---|
| 1 | 0.45% | 0.16% | 748 | 190 |
| 2 | 0.9% | 0.16% | 221 | 340 |
| 3 | 1.5% | 0.16% | 71 | 530 |
| 4 | 2.5% | 0.16% | 12 | 850 |

As can be understood, the addition of an excess amount of electrolyte significantly reduces the viscosity of the acrylic acid polymer containing composition. It was found (see Example 2) that upon injection, this excess will dilute from the composition into the surrounding tissue, thereby increasing the viscosity of the composition to become even a gel. Such a gel will remain at the injection site to await slow diffusion and degradation of its constituents.

EXAMPLE 2

This example pertains to the physical properties of a composition according to the invention, in particular its gel-formation after injection and its release of dispersed content, and its safety upon injection into animal tissue.

In this experiment four pigs were used. Each pig received 1 ml of a composition containing 1.6% Carbopol 974P, 2.5% sodium chloride and 0.48% calcium chloride (having an approximate osmolarity of 925 mOsmol/l) by intramuscular injection. For diagnostic purposes, the formulation additionally comprised 0.075% of the colorant patent blue. Pig number 1 was euthanized 2 hours after injection of the formulation and immediately the muscular tissue was opened to examine the site of administration. A clear spot was visible containing a jelly blue substance. A spoon was taken and the spot could be removed as a gel. The gel did not flow. Pig number 2 was euthanized 24 hours after administration of the same composition, and its muscular tissue was also opened to examine the site of administration. A clear colourless gel could be spotted at the site of administration, which is an indication of diffusion of the patent blue into the body of the pig. Pig number 3 was euthanized after 48 hours, and pig number 4 after one week. From none of these pigs a gel could be isolated. The blue color was disappeared completely.

These results indicate that a gel is present up to 2 days after injection. Small molecules diffuse from the gel within 1 day. It is expected that release of large molecules like proteins is slowed down for about 2 days in this particular formulation.

The local reactions (i.e. spots comprising deviations in the normal tissue) were also scored at the different time points. The results, size of the spots with deviations, are listed below in Table 3. It is noted that the deviations after 2 hours are mainly restricted to the jelly-spot itself. After 24 hours some deviations in a slightly larger tissue volume (5 cm³) were seen, but at a safe (acceptable) level. After 1 week, the remaining spot with deviations was virtually gone. The live pigs did not show any signs of local reactions (like stress, itching, redness, biting etc.). Based on these results it can be concluded that the composition, despite the fact that the osmolarity is about three times the osmolarity of a 0.9% sodium chloride solution, can be regarded as safe.

TABLE 3

Size of the local reaction after IM injection

| Time after vaccination (hr) | Size (length * width * height in cm) | Volume (cm³) |
|---|---|---|
| 2 | 4 * 1 * 1 | 4 |
| 24 | 5 * 2 * 0.5 | 5 |
| 48 | 3 * 2 * 0.5 | 1.5 |
| 168 | 1 * 0.2 * 0.3 | 0.6 |

EXAMPLE 3

Various compositions were made comprising different biological antigens and different types and amounts of acrylic acid polymers. The amount of acrylic acid polymer in each case was at least 0.8% w/w to ensure a high viscosity after injection. The general constitution of each composition is indicated in table 4. It is noted that the indicated viscosity is the viscosity before injection. After injection, the electrolyte will dilute fast from the formulation, whereupon the formulation will become highly viscous and may remain as a stable gel at the site of administration.

TABLE 4

General constitution of compositions containing biological antigens per 1000 grams composition

| Component | type "0.8" (viscosity ± 40 cP) | type "1.6" (viscosity ± 70 cP) |
|---|---|---|
| acrylic acid polymer | 8.0 gr | 16 gr |
| CaCl₂•2H₂O | 1.6 gr | 4.8 gr |
| NaCl | 9.0 gr | 25 gr |
| Antigen | x Units (depending on antigen) | x Units (depending on antigen) |
| Water | added to reach 1000 gr | added to reach 1000 gr |

In general two types of acryl acid polymer comprising formulations were made, the 0.8 type containing 0.8% acrylic acid polymer and the 1.6 type containing 1.6% acrylic acid polymer. In order to keep the viscosity of the compositions sufficiently low to enable injecting of the composition with a standard hypodermic syringe, electrolyte was added as indicated here-above in Table 4. Two different types of cross-linked acrylic acid polymers were used, viz. Carbopol 974P and Carbopol 971 P (both obtainable from BFGoodrich). Various types of antigens were being used, derived from the bacteria *Actinobacillus pleuropneumoniae, Haemophilis parasuis, Mycoplasma hyopneumoniae* and porcine circo virus 2 (PCV2). With these antigens, the following compositions were made:

1 Mhyo/PCV2 Composition

The first composition (denoted "A") comprised the acrylic acid polymer Carbopol 974P in a concentration of 0.8%. In this composition inactivated *Mycoplasma hyopneumoniae* antigens (the same antigens as present in the commercially available vaccine Porcilis Mhyo, available from Intervet Schering-Plough Animal Health, Boxmeer, The Netherlands, in the same concentration) and PCV antigens (the same antigens as present in the commercially available vaccine Porcilis PCV, available from Intervet Schering-Plough Animal Health, Boxmeer, in the same concentration).

The second composition (denoted "B") comprised the acrylic acid polymer Carbopol 971 P in a concentration of 0.8%. In this composition inactivated *Mycoplasma hyopneumoniae* antigens (the same antigens as present in the commercially available vaccine Porcilis Mhyo, available from Intervet Schering-Plough Animal Health, Boxmeer, in the same concentration) and PCV antigens (the same antigens as present in the commercially available vaccine Porcilis PCV, available from Intervet Schering-Plough Animal Health, Boxmeer, in the same concentration).

As a first reference composition a composition denoted "C" was made comprising the same antigens in the same concentration but formulated in the adjuvant emulsion Emunade, as used in the commercially available vaccine M+Pac, available from Intervet Schering-Plough Animal Health, Summit, N.J., USA. A strict control formulation "D" was made consisting merely of PBS solution.

2 APP Composition

A first composition (denoted "E") comprised the acrylic acid polymer Carbopol 974P in a concentration of 0.8%. This composition comprised the same *Actinobacillus hyopneumoniae* antigens (viz. APXI, APX II, APXIII and OMP), in the same amount, as present in the commercially available vaccine Porcilis APP, available from Intervet Schering-Plough Animal Health, Boxmeer, The Netherlands.

As a reference composition, the commercially available vaccine Porcilis APP (denoted as "F") was used.

3 *Haemophilus parasuis* Composition

A first composition (denoted "G") comprised the acrylic acid polymer Carbopol 974P in a concentration of 0.8%. This composition comprised the same *Haemophilus parasuis* antigens (viz. inactivated cells of *Haemophilus parasuis* bacteria), in the same amount, as present in the commercially available vaccine Porcilis Glässer, available from Intervet Schering-Plough Animal Health, Boxmeer, The Netherlands.

As a reference composition, the commercially available vaccine Porcilis Glässer (denoted as "H") was used.

The compositions A, B, E and G were made by firstly making a solution of the electrolytes in about 70% of the required amount of water. After that the acrylic acid polymer was added and mixed until the polymer is completely hydrated. Then the pH of the solution was set to 7.2 using drops of a 4M NaOH solution. This product was autoclaved for 20 minutes at 121° C. Then, the product was cooled to approximately 20° C. while stirring, after which the pH was checked and adjusted if necessary. Then the antigens were added while stirring, after which the pH was again checked and adjusted if necessary. The remaining amount of water was added. The product was stirred overnight before filling the containers, and after filling, was stored in a nitrogen gas atmosphere at 2-8° C.

EXAMPLE 4

In the vaccination experiment, four groups of 10 piglets each were used. The compositions A, B, C and D were administered intramuscularly as a 2 ml dose at three weeks of age. Rectal temperatures were measured just before vaccination (t=0 hr) and 4 hours post vaccination (expected maximum temperature rise).

The following results were obtained. No clinical signs of disease where seen in any of the groups which means that all compositions can be regarded as safe. The average temperatures measured are depicted in Table 5.

TABLE 5

Average temperature after single administration of Mhyp/PCV vaccines

| Composition | $T_{av}$ in ° C. at t = 0 hr | $T_{av}$ in ° C. at t = 4 hr | $\Delta T$ in ° C. |
|---|---|---|---|
| A | 39.8 | 39.6 | −0.2 |
| B | 39.8 | 39.9 | +0.1 |
| C | 39.6 | 40.3 | +0.7 |
| D (strict control) | 39.7 | 39.5 | −0.2 |

As can be seen, the antigens used may give rise to significant temperature rise in vaccinated animals (see results with composition C). However, when formulated according to the invention, the temperature rise may be lower and even completely suppressed.

Next to temperature rise, the antibody titres against the antigens were measured, 6 weeks after administration of the composition. The results are indicated in Table 6.

TABLE 6

Average titres at 6 weeks after single administration of Mhyp/PCV vaccines

| Composition | Average Mhyo titre | Average PCV titre |
|---|---|---|
| A | 0.21 | 10.1 |
| B | 0.12 | 9.2 |
| C | 0.06 | 7.0 |
| D (strict control) | 0.02 | <3.4 |

It is noted that composition C is a vaccine that confers protection against Mhyo since the Mhyo-part is the same as the commercially available single shot vaccine M+Pac. It is thus expected that compositions A and B also confer protection against pathogenic *Mycoplasma hyopneumoniae*. With regard to PCV2, it is known that the commercially available vaccine Porcilis PCV gives rise to protection when the titre is above 9 at about 6 weeks after administration (see i.a EP 2 291 195, results of Example 3).

EXAMPLE 5

Twenty pigs were used at the age of 5½-6 weeks. They were randomly assigned to two treatment groups of ten pigs each. The pigs received compositions E and F respectively at 6 and 10 weeks of age. The animals were observed for systemic reactions, in particular rectal temperature and clinical signs, and local reactions after both vaccinations. Blood sampling was done at 6, 10, 13 and 23 weeks of age for the determination of the serological responses to the vaccines. At the age of 23 weeks animals were post-mortem investigated for local reactions of the injection sites.

With regard to the latter, at slaughter no unacceptable local reactions were seen at the injection sites. The average temperature rise was established 4, 6 and 8 hours after administration of the compositions. The results are depicted in Table 7.

TABLE 7

Average temperature rise after administration of APP vaccines

| | first vaccination (prime) | | | second vaccination (boost) | | |
|---|---|---|---|---|---|---|
| Composition | $\Delta T_{av}$, t = 4 | $\Delta T_{av}$, t = 6 | $\Delta T_{av}$, t = 8 | $\Delta T_{av}$, t = 4 | $\Delta T_{av}$, t = 6 | $\Delta T_{av}$, t = 8 |
| E | 0.8 | 0.8 | 0.6 | 0.5 | 0.5 | 0.1 |
| F | 0.8 | 0.7 | 0.7 | 0.7 | 1.0 | 1.1 |

As can be seen, the antigens used may give rise to significant temperature rise in vaccinated animals (see booster results with composition F). However, when formulated according to the invention, the temperature rise may be lower and even completely suppressed (in particular see results at t=8 hr after booster vaccination).

Next to temperature rise, the antibody titres against the antigens were measured, 13 weeks after administration of the composition. The results are indicated in Table 8.

TABLE 8

Average titres at 13 weeks after administration of APR vaccines

| Composition | APXI | APXII | APXIII | OMP |
|---|---|---|---|---|
| E | 9.7 | 11.0 | 9.7 | 9.5 |
| F | 8.5 | 10.0 | 8.5 | 8.3 |

Given the fact that the composition according to the invention (composition E) even induces higher titers than the commercially available and commonly regarded effective vaccine Porcilis APP (composition F), shows that the new composition is an effective vaccine to protect animals against an infection with pathogenic *Actinobacillus pleuropneumoniae* bacteria.

EXAMPLE 6

In the vaccination experiment, two groups of 6 piglets were used. The compositions G and H were administered intramuscularly as a 2 ml dose at one (prime) and four weeks of age (boost). Rectal temperatures were measured just before vaccination (t=0 hr) and 6 hours post vaccination (expected maximum temperature rise).

No clinical signs of disease were seen in any of the groups which means that all compositions can be regarded as safe. The average temperature rise (t=6 vs t=0 hr) is depicted in Table 9.

TABLE 9

Average temperature rise after administration of *H. parasuis* vaccines

| Composition | first vaccination (prime) $\Delta T_{av}$, t = 6 hr | second vaccination (boost) $\Delta T_{av}$, t = 6 hr |
|---|---|---|
| G | 0.6 | 0.9 |
| H | 0.8 | 1.7 |

As can be seen, the antigens used may give rise to significant temperature rise in vaccinated animals (see in particular the booster result with composition H). However, when formulated according to the invention, the temperature rise may be significantly lower.

Next to temperature rise, the antibody titres against the antigens were measured, 6 weeks after administration of the composition. The results are indicated in Table 10.

TABLE 10

Average titres at 6 weeks after administration of *H. parasuis* vaccines

| Composition | Average HPS titre |
|---|---|
| G | 8.1 |
| H | 8.1 |

Given the fact that the composition according to the invention (composition G) induces the same titer as the commercially available and commonly regarded effective vaccine Porcilis Glässer (composition H), shows that the new composition is an effective vaccine to protect animals against an infection with pathogenic *Haemophilus parasuis* bacteria.

EXAMPLE 7

This example describes further compositions according to the invention and a method of formulating these compositions. These compositions are depicted in Table 11. The table indicates units per 1000 ml of composition.

With regard to the antigens mentioned, the Mhyo antigens are the same antigens as present in the commercially available vaccine Porcilis Mhyo, available from Intervet Schering-Plough Animal Health, Boxmeer, The Netherlands, in the same concentration per dose (1 U/dose). The PCV antigens are the same antigens as present in the commercially available vaccine Porcilis PCV, available from Intervet Schering-Plough Animal Health, Boxmeer, in the same concentration per dose (5E3 U/dose). The *Lawsonia* antigens are the numbers of killed whole cells. The resulting vaccine is for use as a one-shot vaccine, 1 ml per dose, to protect pigs against an infection with porcine circo virus type 2, *Mycoplasma hyopneumoniae* and *Lawsonia intracellularis*. The vaccine is suitable for use in pigs of an age of three days and older. It is believed that no site reactions occur, in particular for the formulations A, B and C.

TABLE 11

Compositions comprising PCV, Mhyo and *Lawsonia* antigens.

| Component | Comp. A | Comp. B | Comp. C | Comp. D | units |
|---|---|---|---|---|---|
| WFI | 118.68 | 237.36 | 356.04 | 474.72 | gram |
| CaCl2 × 2H2O | 1.20 | 2.40 | 3.60 | 4.80 | gram |
| NaCl | 6.25 | 12.50 | 18.75 | 25.00 | gram |
| Carbopol 974P | 4.00 | 8.00 | 12.00 | 16.00 | gram |
| NaOH | 2.07 | 4.14 | 6.21 | 8.28 | gram |
| Mhyo | 1000 | 1000 | 1000 | 1000 | U |
| PCV2 | 5x10E6 | 5x10E6 | 5x10E6 | 5x10E6 | U |
| *Lawsonia* | 1x10E11 | 1x10E11 | 1x10E11 | 1x10E11 | cells |
| Ad WFI until | 1007 | 1015 | 1021 | 1029 | grams |
| Osmolarity | 420 | 550 | 800 | 1100 | mOs/l |

A suitable procedure to constitute the formulations A to D as mentioned in Table 11 is as follows:
1. Add the WFI to the vessel.
2. Make a solution of the sodium chloride and calcium chloride.
3. Add the carbopol. Mix the content till a homogeneous suspension is obtained.
4. Adjust the pH of the solution to around 7 (6.9-7.1) with sodium hydroxide pellets and if necessary re-adjust with hydrochloric acid (4M).
5. Autoclave the product for 20 min at 121° C.
6. Cool the product to 20° C. (15-25).
7. Check the pH and adjust if necessary.
8. Add the antigens while stirring.
9. Check the pH and adjust if necessary
10. Add the remaining amount of water for injection.
11. Store the product at 2-8° C.

The invention claimed is:

1. An aqueous composition containing a biological antigen and an acrylic acid polymer;
    wherein said composition comprises an electrolyte to provide an osmolarity higher than the osmolarity of a 0.9% (w/v) sodium chloride solution in water; and
    wherein the osmolarity of said composition is at least 30% higher than the osmolarity of a 0.9% (w/v) sodium chloride solution.

2. The composition according to claim 1, wherein the osmolarity of the composition is at least 50% higher than the osmolarity of a 0.9% (w/v) sodium chloride solution.

3. The composition according to claim 1, wherein the composition comprises more than 0.2% (w/w) of the acrylic acid polymer.

4. The composition according to claim 3, wherein the composition comprises more than 0.5% (w/w) of the acrylic acid polymer.

5. The composition according to claim 4, wherein the composition comprises between 0.8% and 1.6% (w/w) of the acrylic acid polymer.

6. The composition according to claim 1, wherein the acrylic, acid polymer is a cross linked polymer.

7. The composition according to claim 6, wherein the acrylic acid polymer is cross linked using a polyalkenylether, a polyalcohol and/or a divinylglycol.

8. The composition according to claim 1, wherein the composition comprises an electrolyte comprising a multicharged cation.

9. The composition according to claim 8, wherein the cation is present in a concentration up to 0.05 M.

10. The composition according to claim 1, wherein the biological antigen is an antigen that upon administration induces fever.

11. The composition according to claim 10, wherein the antigen is chosen from the group consisting of a gram-negative bacterium antigen and a circo virus antigen.

12. The composition according to claim 10, wherein the antigen is chosen from the group consisting of *Actinobacillus pleuropneumoniae* antigen, *Haemophilus parasuis* antigen and porcine circo virus 2 antigen.

13. The composition according to claim 1, containing porcine circo virus 2 antigen and *Mycoplasma hyopneumoniae* antigen for use as a vaccine that after one single administration provides an adequate immune response against an infection with porcine circo virus 2 and optionally *Mycoplasma hypneumoniae*.

14. An injectable composition comprising an aqueous composition, containing a biological antigen and an acrylic acid polymer;
   wherein said aqueous composition comprises an electrolyte to provide an osmolarity higher than the osmolarity of a 0.9% (w/v) sodium chloride solution in water;
   wherein the osmolarity of said aqueous composition is at least 30% higher than the osmolarity of a 0.9% (w/v) sodium chloride solution; and
   wherein said injectable composition has a viscosity of less than 200 mPa·s.

15. The composition according to claim 9, wherein the cation is present in a concentration up to 0.03 M.

* * * * *